(12) United States Patent
Davuluri et al.

(10) Patent No.: US 8,940,749 B2
(45) Date of Patent: Jan. 27, 2015

(54) PREPARATION OF 3-[2-[4-((6-FLUORO-1, 2-BENZISOXAZOL-3-YL)-L-PIPERIDINYL)-6, 7, 8, 9-TETRAHYDOR-9-HYDROXY-2-METHYL-4H-PYRIDO[ 1, 2-A]-PYRIMIDIN-4-ONE(PALIPERIDONE) AND PALIPERIDONE PALMITATE

(76) Inventors: Ramamohan Rao Davuluri, San Clemente, CA (US); Ravi Ponnaiah, Hyderabad (IN); Praveen Kumar Neela, Hyderabad (IN); Guruswamy Batthini, Hyderabad (IN); Telagareddy Venkata Narasimharao, Hyderabad (IN); Kosireddy Ravanababu, Hyderabad (IN); Kallepally Sudheer, Nalgonda (IN)

( * ) Notice: Subject to any disclaimer, the term of this patent is extended or adjusted under 35 U.S.C. 154(b) by 28 days.

(21) Appl. No.: 13/819,372

(22) PCT Filed: May 30, 2012

(86) PCT No.: PCT/IN2012/000375
§ 371 (c)(1),
(2), (4) Date: Feb. 27, 2013

(87) PCT Pub. No.: WO2012/164582
PCT Pub. Date: Dec. 6, 2012

(65) Prior Publication Data
US 2014/0073787 A1    Mar. 13, 2014

(30) Foreign Application Priority Data
May 31, 2011   (IN) .......................... 1854/CHE/2011

(51) Int. Cl.
*C07D 471/04*    (2006.01)

(52) U.S. Cl.
CPC .................................. *C07D 471/04* (2013.01)
USPC ................... 514/259.4; 514/259.41; 544/282

(58) Field of Classification Search
CPC ..................................................... C07D 471/04
USPC ........................... 514/259.4, 259.41; 544/282
See application file for complete search history.

(56) References Cited

U.S. PATENT DOCUMENTS 5,254,556 A * 10/1993 Janssen et al. ........... 514/259.41

* cited by examiner

*Primary Examiner* — Erich A Leeser
(74) *Attorney, Agent, or Firm* — Schmeiser, Olsen & Watts, LLP

(57) ABSTRACT

An improved process for the synthesis of 3-[2-[4-((6-fluoro-1,2-benzisoxazol-3-yl)-1-piperidinyl]-6,7,8,9-tetrahydro-9-hydroxy-2-methyl-4H-pyrido[1,2-a]-pyrimidin-4-one (Paliperidone) and Paliperidone Palmitate through a novel intermediate (2-Chloroethyl)-6,7,8,9-tetrahydro-2-methyl-9-hydroxy-4H-pyrido [1,2-a]pyrimidine-4-one Palmitate ester.

13 Claims, No Drawings

PREPARATION OF 3-[2-[4-((6-FLUORO-1,2-BENZISOXAZOL-3-YL)-L-PIPERIDINYL)-6,7,8,9-TETRAHYDOR-9-HYDROXY-2-METHYL-4H-PYRIDO[1,2-A]-PYRIMIDIN-4-ONE(PALIPERIDONE) AND PALIPERIDONE PALMITATE

CROSS REFERENCE TO RELATED APPLICATION

This application claims priority from the provisional specification No. 1854/CHE/2011 filed on May 31, 2011.

FIELD OF THE INVENTION

The present invention encompasses process for the preparation of Paliperidone and Paliperidone Palmitate through a novel intermediate.

BACKGROUND OF THE INVENTION

Paliperidone is chemically known as 3-[2-[4-(6-fluoro-1,2-benzisoxazol-3-yl)-1-piperidinyl]ethyl]-6,7,8,9-tetrahydro-9-hydroxy-2-methyl-4Hpyrido[1,2-a]pyrimidin-4-one, is a 5-HT antagonist and belonging to the chemical class of benzisoxazole derivatives and having the following structural formula:

Formula VIII

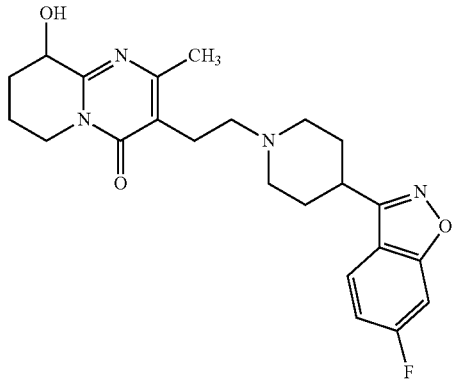

Paliperidone ("PLP") is a metabolite of Risperidone. Marketed under the trade name Invega, Paliperidone is an antipsychotropic agent approved in the United States for the treatment of schizophrenia.

The Palmitate ester of Paliperidone can be chemically named as 3-[2-[4-(6-fluoro-1,2-benzoisoxazol-3-yl)-1-piperidyl]ethyl]-6,7,8,9-tetrahydro-9-hydroxy-2-methyl-4H-pyrido[1,2-a]pyrimidin-4-one Palmitate ester and has the following formula:

Formula VII

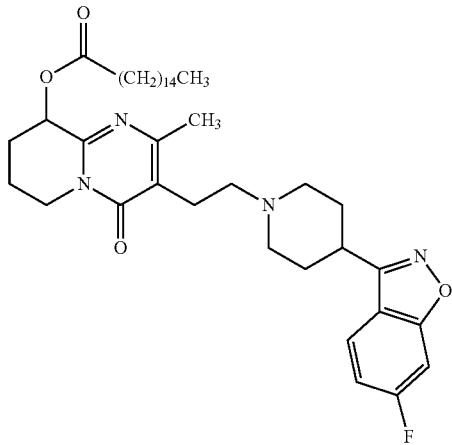

Paliperidone Palmitate ("PLP-P") is described in U.S. Pat. Nos. 5,158,952 and 5,254,556. US '556 disclose processes for the preparation of both the decanoyl and the acetyl derivatives of Paliperidone Palmitate.

Other process for the preparation of PLP-P are described in U.S. Pat. No. 6,077,843 and US Patent Application No. 20080214808.

SUMMARY OF THE INVENTION:

The present invention is an improved process for the synthesis of 3-[2-[4-((6-fluoro-1,2-benzisoxazol-3-yl)-1-piperidinyl]-6,7,8,9-tetrahydro-9-hydroxy-2-methyl-4H-pyrido[1,2-a]-pyrimidin-4-one (Paliperidone) and Paliperidone Palmitate through a novel intermediate (2-Chloroethyl)-6,7,8,9-tetrahydro-2-methyl-9-hydroxy-4H-pyrido[1,2-a]pyrimidine-4-one Palmitate ester.

In one of the embodiment, the present invention encompasses a process for preparing 3-(2-chloroethyl)-6,7,8,9-tetrahydro-2-methyl-9-hydroxy-4H-pyrido[1,2-a]pyrimidine-4-one Palmitate ester which is a novel intermediate used in the synthesis of Paliperidone and Paliperidone Palmitate.

In another embodiment, the present invention encompasses a process for preparing Paliperidone Palmitate comprising of combining 3-(2-chloroethyl)-6,7,8,9-tetrahydro-2-methyl-9-hydroxy-4H-pyrido[1,2-a]pyrimidine-4-one with fatty acid in presence of at least one organic or inorganic base, a pyridine derivative and at least one organic solvent to obtain a reaction mixture, adding acid halide to mixture and maintaining the mixture for time sufficient to give a novel intermediate of compound 3-(2-chloroethyl)-6,7,8,9-tetrahydro-2-methyl-9-hydroxy-4H-pyrido[1,2-a]pyrimidine-4-one Palmitate ester. 3-(2-chloroethyl)-6,7,8,9-tetrahydro-2-methyl-9-hydroxy-4H-pyrido[1,2-a]pyrimidine-4-one Palmitate ester combines with 6-fluoro-3-(4-piperidinyl)-1,2-benzisoxazole or its mono-hydrochloride in organic solvent in presence of base such as alkali metal carbonates or bicarbonates, organic metals, metal carbonates, metal bicarbonates, metal hydroxides or organic bases such as isopropyl amine, diisopropylamine, diisopropyl ethyl-amine, N-methyl morpholine, N-methyl piperidine, N-methyl piperazine, N-methyl pyridine, DBU, DABCO, triethylamine etc. to form a reaction mixture and maintaining the mixture for sufficient time to give a compound Paliperidone Palmitate.

In yet another embodiment, the present invention encompasses a process for preparing Paliperidone through a novel intermediate of compound 3-(2-chloroethyl)-6,7,8,9-tetrahydro-2-methyl-9-hydroxy-4H-pyrido[1,2-a]pyrimidine-4-one Palmitate ester.

The main objective of the present invention is to provide an improved process for the preparation of Paliperidone and Paliperidone Palmitate through a novel intermediate with high purity and high yield.

DETAIL DESCRIPTION OF THE INVENTION

The present invention involves a process for the preparation of Paliperidone and Paliperidone Palmitate through a novel intermediate 3-(2-chloroethyl)-6,7,8,9-tetrahydro-2-methyl-9-hydroxy-4H-pyrido[1,2-a]pyrimidine-4-one Palmitate ester. The process of the invention is depicted in following Scheme-I.

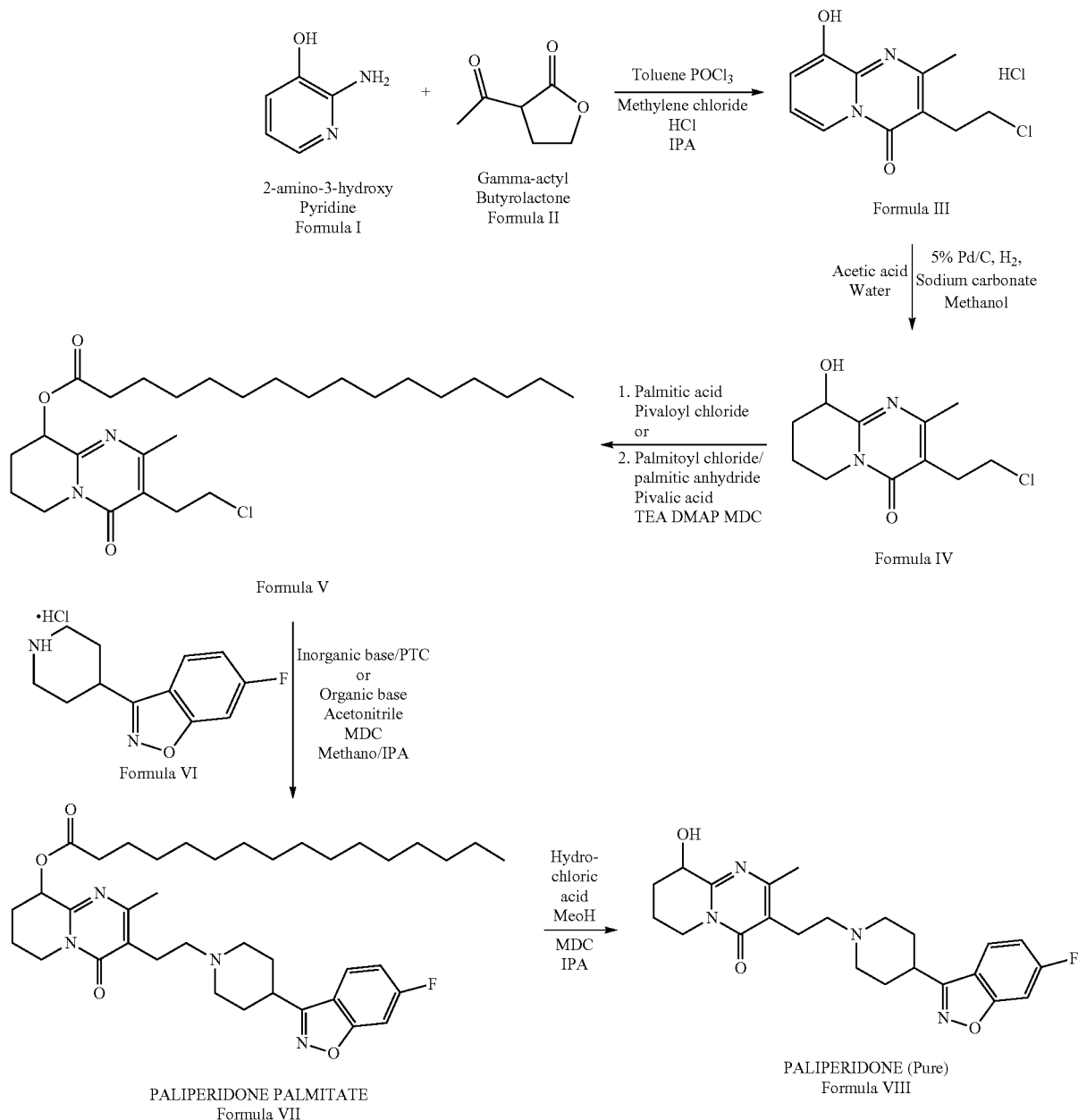

PALIPERIDONE PALMITATE
Formula VII

PALIPERIDONE (Pure)
Formula VIII

Starting material of the present invention that is 3-(2-chloroethyl)-6,7,8, 9-tetrahydro-2-methyl-9-hydroxy-4H-pyrido[1,2-a]pyrimidine-4-one can be prepared according to any methods known in the art, for example according to U.S. Pat. No. '952.

The present invention involves a process for the preparation of 3-(2-chloroethyl)-6,7,8,9-tetrahydro-2-methyl-9-hydroxy-4H-pyrido[1,2-a]pyrimidine-4-one Palmitate ester of Formula V comprising: combining 3-(2-chloroethyl)-6,7,8,9-tetrahydro-2-methyl-9-hydroxy-4H-pyrido[1,2-a]pyrimidine-4-one with fatty acid in presence of a pyridine derivative, at least one organic or inorganic base and at least one organic solvent to form a reaction mixture, adding acid halide to reaction mixture and maintaining the mixture for 2-3 hrs to give a compound 3-(2-chloroethyl)-6,7,8,9-tetrahydro-2-methyl-9-hydroxy-4H-pyrido[1,2-a]pyrimidine-4-one Palmitate ester.

The compound Formula V can also be prepared by the process comprising of combining 3-(2-chloroethyl)-6,7,8,9-tetrahydro-2-methyl-9-hydroxy-4H-pyrido[1,2-a]pyrimidine-4-one with fatty acid in presence of a N,N'-dicyclo hexylcarbodiimide, catalytic amount of pyridine derivative, at least one organic or inorganic base and at least one organic solvent to form a reaction mixture and maintaining the mixture for sufficient period of time at room temperature to give the compound 3-(2-chloroethyl)-6,7,8,9-tetrahydro-2-methyl-9-hydroxy-4H-pyrido[1,2-a]pyrimidine-4-one Palmitate ester (Formula V).

The compound Formula V can also be prepared using (2-chloroethyl)-6,7,8,9-tetrahydro-2-methyl-9-hydroxy-4H-pyrido[1,2-a]pyrimidine-4-one alkoxide as an intermediate.

The process for preparing (2-chloroethyl)-6,7,8,9-tetrahydro-2-methyl-9-hydroxy-4H-pyrido[1,2-a]pyrimidine-4-one alkoxide comprising: combining (2-chloroethyl)-6,7,8,9-tetrahydro-2-methyl-9-hydroxy-4 H-pyrido[1,2-a]pyrimidine-4-one with at least one organic solvent to obtain a suspension, adding at least one base to the suspension to obtain a reaction mixture and maintaining the mixture for sufficient period of time to give (2-chloroethyl)-6,7,8,9-tetrahydro-2-methyl-9-hydroxy-4H-pyrido[1,2-a]pyrimidine-4-one alkoxide which further combines with palmitoyl chloride in presence of at least one organic solvent to obtain a reaction mixture and maintaining the mixture for sufficient period of time to give 3-(2-chloroethyl)-6,7,8,9-tetrahydro-2-methyl-9-hydroxy-4H-pyrido[1,2-a]pyrimidine-4-one Palmitate ester of Formula V.

The fatty acid is selected from the group consisting of palmitic acid, palmitoyl chloride and palmitic anhydride. But preferably, the fatty acid used is palmitic acid.

The pyridine derivative used is 4-dimethyl amino pyridine.

The base may be selected from organic base or inorganic base, wherein the organic base is selected from the group consisting of isopropyl amine, diisopropyl amine, diisopropyl ethyl-amine, N-methyl morpholine, N-methyl piperidine, N-methyl piperazine, N-methyl pyridine, DBU, DABCO and triethylamine. Inorganic base may be selected from the group consisting of alkali metals like sodium, potassium, lithium or alkali metal carbonates like sodium carbonate, potassium carbonate, cesium carbonate, lithium carbonate or alkali metal bicarbonates like sodium bicarbonate, potassium bicarbonate, lithium bicarbonate, cesium bicarbonate or alkali metal hydroxides like sodium hydroxide, calcium hydroxide, potassium hydroxide or metal alkoxides like alkoxides of sodium, lithium or potassium, sodium tert-butoxide and sodium hydride. But preferably, the base used is triethylamine.

The organic solvent is selected from the group consisting of methylene chloride, acetonitrile, dimethyl sulfoxide (DMSO), dimethyl amine (DMA), $C_3$-$C_6$ amides like dimethyl acetamide and dimethyl form-amide, $C_2$-$C_6$ alkylacetates are ethyl acetates and isobutyl acetate, $C_2$-$C_8$ ethers or $C_4$-$C_8$ ethers are tetrahydrofuran (THF), diethoxymethane (DEM), isobutyl methyl ether, dibutyl ether and polyethylene glycol methyl ether (PGME), $C_4$-$C_{10}$ cyclic or acyclic ethers, $C_2$-$C_4$ diols, dimethyl carbonate, diethyl carbonate, $C_3$-$C_6$ ketones like acetone, methyl ethyl ketone, methyl isobutyl ketone, $C_5$-$C_{12}$ cyclic or acyclic hydrocarbons, $C_6$-$C_{12}$ aromatic hydrocarbons like benzene, toluene, o-xylene, m-xylene and p-xylene. Preferably, the organic solvent used may be acetonitrile, dichloromethane, toluene, DMF, DMA or DMSO. Most preferably, the organic solvent used is methylene chloride.

The acid halides are selected from the group consisting of acetyl chloride, pivaloyl chloride, benzoyl chloride, methane sulfonyl chloride, toluene sulphonyl chloride and thionyl chloride. Preferably, acid chloride used is pivaloyl chloride.

In another embodiment, the present invention involves a process for preparing Paliperidone Palmitate by combining 3-(2-chloroethyl)-6,7,8,9-tetrahydro-2-methyl-9-hydroxy-4H-pyrido[1,2-a]pyrimidine-4-one Palmitate ester of Formula V with 6-fluoro-3-(4-piperidinyl)-1,2-benzisoxazole mono-hydrochloride of Formula VI in the presence of polar aprotic solvent, alkali metal carbonate or metal bicarbonates or alkali hydroxides, alkali halides and phase transfer catalyst to form a reaction mixture and maintaining the reaction mixture for 20 hrs at 80° C. to obtain the compound Paliperidone Palmitate of Formula VII.

The organic solvent is selected from water, methanol, ethanol, propanol, isopropanol, 1-butanol, dichloromethane, chloroform, 1,2-dichloroethane, diethylether, diisopropyl ether, benzene, methyl-benzene, dimethylbenzene, chlorobenzene, methoxy benzene, methanol, ethanol, 1-butanol, 2-propanone, 4-methyl-2-pentanone, tetrahydrofuran, 1,4-dioxane, N,N-dimethylformamide, N,N-dimethylacetamide, dimethylsulfoxide, pyridine, nitrobenzene, acetonitrile, or propionitrile. Preferably the solvent used is acetonitrile.

The base may be selected from alkali metal carbonates or metal bicarbonates or alkali hydroxides, wherein the alkali metal carbonates is selected from the group consisting of sodium carbonate, potassium carbonate, alkali metal bicarbonates of sodium bicarbonate, potassium bicarbonate, alkali hydroxides of sodium hydroxide, potassium hydroxide, lithium hydroxide. But preferably, potassium carbonate is used.

The alkali halide is selected from sodium iodide or potassium iodide. Preferably, potassium iodide is used.

The phase transfer catalyst used is selected from the group of tetrabutyl ammonium bromide, tetrabutyl ammonium chloride or tetrabutyl ammonium iodide. Preferably, the phase transfer catalyst used is tetrabutyl ammonium iodide.

The present invention provides a Paliperidone Palmitate having a purity of about 98%, preferably more than 99%, more preferably more than 99.5%.

In yet another embodiment, the present invention involves the preparation of Paliperidone of Formula VIII from Paliperidone Palmitate of Formula VII comprising: combining Paliperidone palmitate with at least one organic solvent, at least one base or mineral acid to form a reaction mixture and maintaining the mixture to reflux for certain period of time to give a pure Paliperidone.

The organic solvent is selected from methanol, ethanol, propanol, butanol, DMF, THF, toluene, water. Preferably, the solvent used is water.

The base is selected from alkali hydroxides such as sodium hydroxide, potassium hydroxide, lithium hydroxide. Preferably, sodium hydroxide is used.

The acid is selected from hydrochloric acid, hydrobromic acid or nitric acid. But preferably, the acid used is hydrochloric acid.

The present invention yields Paliperidone with purity more than 99% and more preferably than 99.5% with Diketone impurity less than 0.1%, with more preferably diketone impurity less than 0.05%.

The invention is further illustrated with the following non-limiting examples.

EXAMPLES

Example 1

Preparation of 3-(2-chloroethyl)-6,7,8,9-tetrahydro-2-methyl-9-hydroxy-4H-pyrido[1,2-a]pyriinidine-4-one Palinitate ester A mixture of methylene chloride, 3-(2-chloroethyl)-6,7,8,9-tetrahydro-2-methyl-9-hydroxy-4H-pyrido[1,2-a]pyrimidine-4-one, palmitic acid, 4-dimethyl amino pyridine and triethylamine was stirred for 15 min at 25-30° C., pivaloyl chloride was added slowly to above reaction mass at 25-40° C. and the reaction was maintained for 2 hours at 30-35° C. then the reaction mass was cooled to 25° C., charged purified water, separated the organic layer, washed the organic layer with dilute hydrochloric acid followed by water, distilled off methylene chloride completely and co distilled with acetonitrile. The resulted residue was dissolved in acetonitrile and added purified water slowly at 25-30° C., stirred the contents for 30 minutes at the same temperature and cooled the mass to 10-15° C. stirred for 2 hours at the same temperature, filtered the isolated compound, washed the wet cake with chilled acetonitrile and dried the compound under vacuum.

Yield: 95% (Theoretical).

Example 2

Preparation of Paliperidone Palmitate

A mixture of acetonitrile, 6-fluoro-3-(4-piperidinyl)-1,2-benzisoxazole mono-hydrochloride, potassium carbonate was stirred for 10 minutes at 25-30° C., heated the reaction mass to 55-60° C. and stirred for 1 hour at the same temperature, cooled the contents to 25-30° C. and added tetra butyl ammonium iodide, potassium iodide and 3-(2-chloroethyl)-6,7,8,9-tetrahydro-2-methyl-9-hydroxy-4H-pyrido[1,2-a]pyrimidine-4-one Palmitate ester at same temperature, heated the reaction mass to 70-75° C. slowly during 2 hours, maintained the reaction for 14 hours and monitored the reaction by HPLC. The reaction mass was cooled to 25-30° C., solvent was distilled off completely under vacuum and the resulted residue was dissolved in methylene chloride, the clear methylene chloride layer was washed with purified water followed by 5% Sodium bicarbonate solution twice and finally methylene chloride layer was washed with purified water, methylene chloride was distilled off completely under vacuum, added methanol to the resulted residue and cooled to 15-20° C. and stirred the contents for 2 hour at the same temperature, filtered the isolated compound, washed with methanol. The wet compound taken in to Isopropyl alcohol and heated the contents to reflux temperature to get clear solution, added activated carbon, maintained for 15 minutes, filtered the carbon through hyflo bed and carbon bed washed with hot Isopropyl alcohol. The filtrate slowly cooled to 25-30° C. and stirred for 2 hours at the same temperature, the isolated compound was filtered and washed with Isopropyl alcohol and dried the at 55-60° C. to get the pure paliperidone palmitate.

Yield: 80% (Theoretical)

Example 3

Preparation of Paliperidone from Paliperidone Palmitate

A mixture of dilute hydrochloric acid and paliperidone palmitate heated to 75-80° C. and the reaction was maintained for 2 hours at 75-80° C., monitored the reaction by HPLC for absence of paliperidone palmitate and cooled the reaction mass to 25-30° C. The reaction mass was washed with methylene chloride, added a mixture of methylene chloride and methanol to aqueous layer, cooled the contents to 10° C., adjusted pH 10-12 with 20% sodium hydroxide in water solution at 10-30° C., extracted the compound into methylene chloride at basic condition and washed the methylene chloride layer with purified water and the separated methylene chloride layer treated with activated carbon, filtered the carbon through hyflow bed, washed with methylene chloride, the methylene chloride was distilled off completely under vacuum and added Isopropyl alcohol, heated the contents to reflux temperature and slowly cooled to 25-30° C., stirred for 1 hour at the same temperature, filtered the isolated compound, washed the wet compound with Isopropyl alcohol and dried under vacuum at 55-60° C. to get pure paliperidone.

Yield: 90% (Theoretical)

We claim:

1. A process for preparing 3-(2-Chloroethyl)-6,7,8,9-tetrahydro-2-methyl-9-hydroxy-4H-pyrido[1,2-a]pyrimidine-4-one Palmitate ester of Formula V Formula V

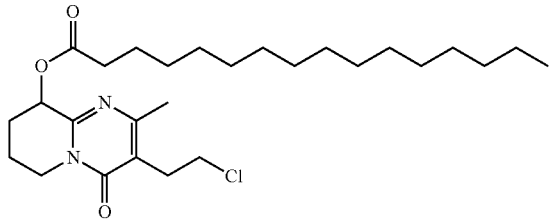

comprising the steps of:
  combining 3-(2-Chloroethyl)-6,7,8,9-tetrahydro-2-methyl-9-hydroxy-4H-pyrido[1,2-a]pyrimidine-4-one with a fatty acid derivative in the presence of a pyridine derivative, at least one base and at least one organic solvent to obtain a reaction mixture; and
  adding an acid halide to the reaction mixture and maintaining the mixture for sufficient time to give the compound 3-(2-chloroethyl)-6,7,8,9-tetrahydro-2-methyl-9-hydroxy-4H-pyrido[1,2-a]pyrimidine-4-one Palmitate ester of Formula V.

2. The process according to claim 1, wherein the fatty acid derivative is selected from the group consisting of palmitic acid, palmitoyl chloride and palmitic anhydride.

3. The process according to claim 1, wherein the pyridine derivative is 4-dimethyl amino pyridine.

4. The process according to claim 1, wherein the base is selected from an organic base or an inorganic base.

5. The process according to claim 1, wherein the acid halide is selected from group consisting of acetyl chloride, pivaloyl chloride, benzoyl chloride, methane sulfonyl chloride, toluene sulphonylchloride and thionyl chloride.

6. The process according to claim 1, wherein the organic solvent is selected from the group consisting of methylene chloride, acetonitrile, dimethyl sulfoxide (DMSO), dimethyl amine (DMA), $C_3$-$C_6$-amides, $C_2$-$C_6$-alkylacetates, $C_2$-$C_8$ethers, $C_4C_{10}$ cyclic ether, $C_4$-$C_{10}$ acyclic ether, $C_2$-$C_4$ diols, dimethyl carbonate, diethyl carbonate,$C_3$-$C_6$ ketones, $C_5$-$C_{12}$ cyclic hydrocarbons, $C_5$-$C_{12}$ acyclic hydrocarbons and $C_6$-$C_{12}$ aromatic hydrocarbons and mixtures thereof.

7. A process for preparing Paliperidone Palmitate of Formula VII,

Formula VII

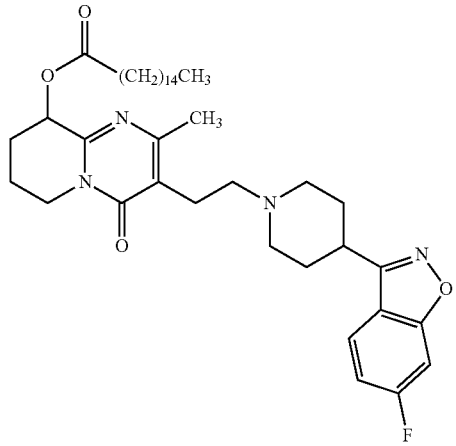

comprising the steps of:
reacting (2-Chloroethyl)-6,7,8,9-tetrahydro-2-methyl-9-hydroxy-4H-pyrido[1,2-a]pyrimidine-4-one palmitate ester compound of Formula V with 6-fluoro-3-(4-piperidinyl)-1,2-benzisoxazole monohydrochloride in the presence of a base in a solvent to give the compound paliperidone palmitate of Formula VII.

8. The process according to claim 7, wherein the solvent is selected from the group consisting of water, methanol, ethanol, propanol, isopropanol, 1-butanol, dichloromethane, chloroform, 1,2-dichloroethane, diethyl ether, diisopropylether, benzene, methyl benzene, dimethyl benzene, chlorobenzene, methoxy benzene, 2-propanone, 4-methyl-2-pentanone, THF, 1,4-dioxane, DMF, DMA, DMSO, nitrobenzene, pyridine, acetonitrile, propionitrile and mixtures thereof.

9. The process according to claim 7, wherein the base is selected from the group consisting of alkali metal carbonate, metal bicarbonate, metal hydroxides and organic bases.

10. The process according to claim 7, wherein the purity of paliperidone palmitate is at least 99%.

11. A compound of Formula V

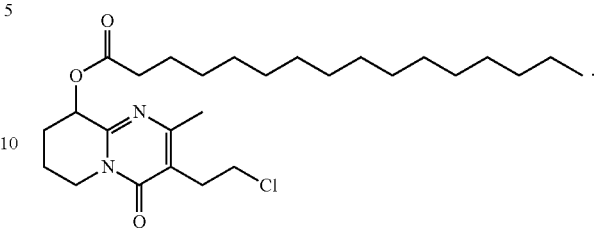

Formula V

12. The process to claim 4, wherein the organic base is selected from the group consisting of isopropyl amine, diispropyl amine, diisoproyl ethyl-amine, N-methylmorpholine, N-methyl piperidine, N-methyl piperazine, N-methyl pyridine, DBU, DABCO and triethylamine.

13. The process according to claim 4, wherein the inorganic base is selected from the group consisting of sodium, potassium, lithium, sodium carbonate, potassium carbonate, cesium carbonate, lithium carbonate, sodium, potassium, lithium, cesium bicarbonates, sodium hydroxide, potassium hydroxide and calcium hydroxide.

* * * * *